United States Patent [19]

Steudle et al.

[11] Patent Number: 4,706,495
[45] Date of Patent: Nov. 17, 1987

[54] METHOD AND APPARATUS FOR THE DETERMINATION OF SUBSTANCES DISSOLVED IN A SOLVENT

[75] Inventors: Ernst Steudle, Jülicher Strasse 28, D-5110 Alsdorf; Josef Zillikens, Jülich; Gerd Böling, Inden-Pier, all of Fed. Rep. of Germany

[73] Assignees: Kernforschungsanlage Jülich Gesellschaft mit beschränkter Haftung, Jülich; Ernst Steudle, Alsdorf, both of Fed. Rep. of Germany

[21] Appl. No.: 793,565

[22] Filed: Oct. 31, 1985

[30] Foreign Application Priority Data

Oct. 31, 1984 [DE] Fed. Rep. of Germany ....... 3439765
Jul. 18, 1985 [DE] Fed. Rep. of Germany ....... 3525668

[51] Int. Cl.$^4$ ............................................. G01N 7/10
[52] U.S. Cl. ................................................... 73/64.3
[58] Field of Search ..................... 73/64.3, 53, 61 R; 210/321.1, 321.2

[56] References Cited

U.S. PATENT DOCUMENTS

| | | | |
|---|---|---|---|
| 3,063,288 | 11/1962 | Reiff | 73/64.3 |
| 3,187,562 | 6/1965 | Rolfson | 73/64.3 |
| 3,526,588 | 9/1970 | Michaels et al. | 210/23 |
| 3,541,005 | 11/1970 | Strathmann et al. | 210/19 |
| 3,567,810 | 3/1971 | Baker | 264/41 |
| 3,615,024 | 10/1971 | Michaels | 210/490 |
| 3,661,011 | 5/1972 | Myrenne | 73/64.3 |
| 4,245,495 | 1/1981 | Kakicuchi et al. | 73/64.3 |
| 4,413,528 | 11/1983 | Hök et al. | 73/753 |
| 4,475,556 | 10/1984 | Reiff | 73/64.3 |
| 4,481,808 | 11/1984 | Sakata et al. | 73/64.3 |

OTHER PUBLICATIONS

Collings et al., A Diaphragm Cell for Diffusion Measurement in Liquid Under Pressure, J. Phys. Eng., (GB) vol. 4, No. 12, 1970.
Hallikaine Instruments, Automatic Osmometer, Shell Development Company (brochure) 2-1964.
Franz, Percutaneous Absorption on the Revelance of in Vetro Data, Journal of Investigative Dermatology, vol. 64, 1975.
"Determination of Permeability Coefficients, Reflection Coefficients, and Hydraulic Conductivity of Chara Corallina using the Pressure Probe: Effects of Solute Concentrations", authored by E. Steudle and S. D. Tyerman (1983), J. Membrane Biology, 75, 85-96.

Primary Examiner—Stewart J. Levy
Assistant Examiner—Hezron E. Williams
Attorney, Agent, or Firm—Nils H. Ljungman

[57] ABSTRACT

The invention relates to methods for the determination of the concentration of substances dissolved in a solution by means of an osmotic cell, using a pressure measurement device, and an apparatus incorporating the aforesaid osmotic cell with pressure measurement device. According to a first method, the concentrations of the substances are determined by the formation of the differences between a final pressure which is established after contact with the solution and an original and minimum pressure. According to a second method, the pressure/time course of biphasic response curves is analyzed in the vicinity of the minimum pressure, along with the rate constant for the exponential pressure increase which takes place after the minimum pressure, and the concentrations of the substances are then computed. According to a third method, simultaneous with one another, the initial slopes of the pressure/time curve of the pressure decrease in two osmotic cells are determined, and from these data, two results are determined, which are functions of the concentrations of the substances, and the concentrations of the substances are calculated from them. The reflection coefficients of both osmotic cells must thereby differ sufficiently.

30 Claims, 13 Drawing Figures

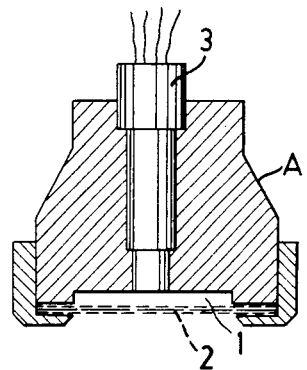
FIG. IA
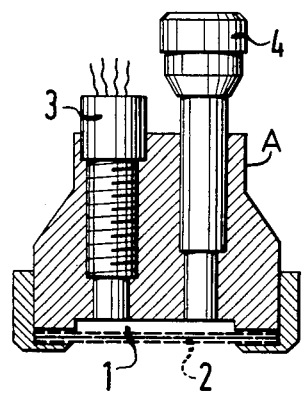
FIG. IB

METHOD AND APPARATUS FOR THE DETERMINATION OF SUBSTANCES DISSOLVED IN A SOLVENT

BACKGROUND OF THE INVENTION

Field of the Invention

The invention relates to a method for the determination of the concentration of substances dissolved in a solvent by means of an osmotic cell with a pressure measurement apparatus for the measurement of the hydrostatic pressure in the osmotic cell, whereby the osmometer solution in the osmotic cell is placed in communication via a membrane with the solution containing the substances. The invention also relates to a measurement head for an apparatus for the determination of the concentration of the substances as well as the related apparatus.

The determination of the concentration of substances in a solution, if there are two or more substances in the solution, is generally difficult and expensive, and is often possible only after a preliminary separation of the substances.

OBJECTS OF THE INVENTION

It is therefore an object of the present invention to provide a process which makes possible the determination of the concentration of a substance, or the concentrations of substances, in a solution in a fast and easy manner, even if there is more than one substance in a solution.

It is a further object of this invention to provide an apparatus with a measurement head for the execution of a method, whereby the concentration of a substance or the concentrations of substances in a solution can be determined.

SUMMARY OF THE INVENTION

The invention provides both an apparatus and a process for the determination of the concentrations of substances dissolved in a solvent by means of an osmotic cell with a pressure measurement apparatus for the measurement of the hydrostatic pressure in the osmotic cell. The invention provides alternative methods for effecting this process.

According to a first method, the concentrations of the substances are determined by establishing the difference between the minimum pressure which is established after contact with solution and the final pressure.

A second method provides a technique whereby the pressure/time course is analyzed around the vicinity of the minimum pressure of biphasic pressure/time curves. Rate constants for water and solute exchange are determined as well along with this method, and the concentrations of the substances are then computed.

According to a third method, the initial slopes of the pressure/time curve of the pressure decrease in two osmotic cells are simultaneously determined. From this data, two results are determined which are functions of the concentrations of the substances. The concentrations of the substances are thus calculated. The reflection coefficients of both osmotic cells must thereby differ sufficiently so that the necessary simultaneous calculations can be made.

Additionally, alternative embodiments of an osmotic cell with a pressure measurement apparatus are disclosed.

BRIEF DESCRIPTION OF THE DRAWINGS

The above, as well as other features and advantages of the present invention, can be more readily appreciated through consideration of the detailed description of the invention in conjunction with the several figures, in which:

FIG. 1A shows a measurement head "A", consisting of an osmotic cell with a pressure measurement apparatus.

FIG. 1B shows a measurement head "A", consisting of an osmotic cell with a pressure measurement apparatus, as well as a micrometer screw with a control rod;

DESCRIPTION OF THE PREFERRED EMBODIMENTS

The invention provides both a method and an apparatus for the determination of the concentration of substances dissolved in a solvent. The apparatus by which the method of this invention can be performed will be initially considered, after which the method will be described in detail.

The measurement head "A" illustrated in FIG. 1 comprises an osmotic cell 1 with a rigid partition of metal or plastic, with a membrane 2 which at least partly forms its outer boundary, and a pressure measurement apparatus 3 with a pressure tranducer which emits electrical signals. An example of such a pressure transducer is found in U.S. Pat. No. 4,413,528, issued on Nov. 8, 1983, which is incorporated herein by reference. The membrane 2 used for the measuring head was obtained from REICHELT CHEMIETECHNIK, Heidelberg, Federal Republic of Germany, under the tradename "THOMAPOR, Reverse Osmosis Membranes". A manufacturer for asymmetrical membrane foils used for reverse osmosis processes is the KALLE Company, a subsidiary of the HOECHST AG, Wiesbaden, Federal Republic of West Germany (Tradename: "NADIR Separation Foils for Hyperfiltration"). The foils consist of a laminate of membrane-forming agent and the backing material, such as paper, polyester fleece, or polypropylene fleece. A metal grid can be disposed on the membrane 2 on the side of the membrane facing away from the osmotic cell 1. Additionally, the membrane 2 can, for example, comprise a hollow fiber acting as a hyperfiltration membrane. There is also an apparatus 4 for the controlled volume change of the osmotic cell 1, comprising a micrometer screw with control rod, by means of which a measurable volume change of the osmotic cell can be made. This controlled volume change, which results in a change in pressure in the osmotic cell, can therefore be used to check the rigidity of the osmotic cell via the pressure measurement apparatus 3 or to determine the modulus of elasticity of the cell. The osmotic cell 1 can also be equipped with an agitation device, such as a magnetic stirrer of the type comprising a small magnet or metallic object disposed within the osmotic cell and manipulated by a rotating magnetic field generated external to the osmotic cell. Such stirrers are known in the art, and are not illustrated herein. Examples of such magnetic stirrers are described in U.S. Pat. Nos. 4,534,656; 4,512,666; 4,498,785; 4,465,377; 4,227,815; 4,162,855; and 4,080,663, which patents are incorporated herein by reference.

Figure 2:
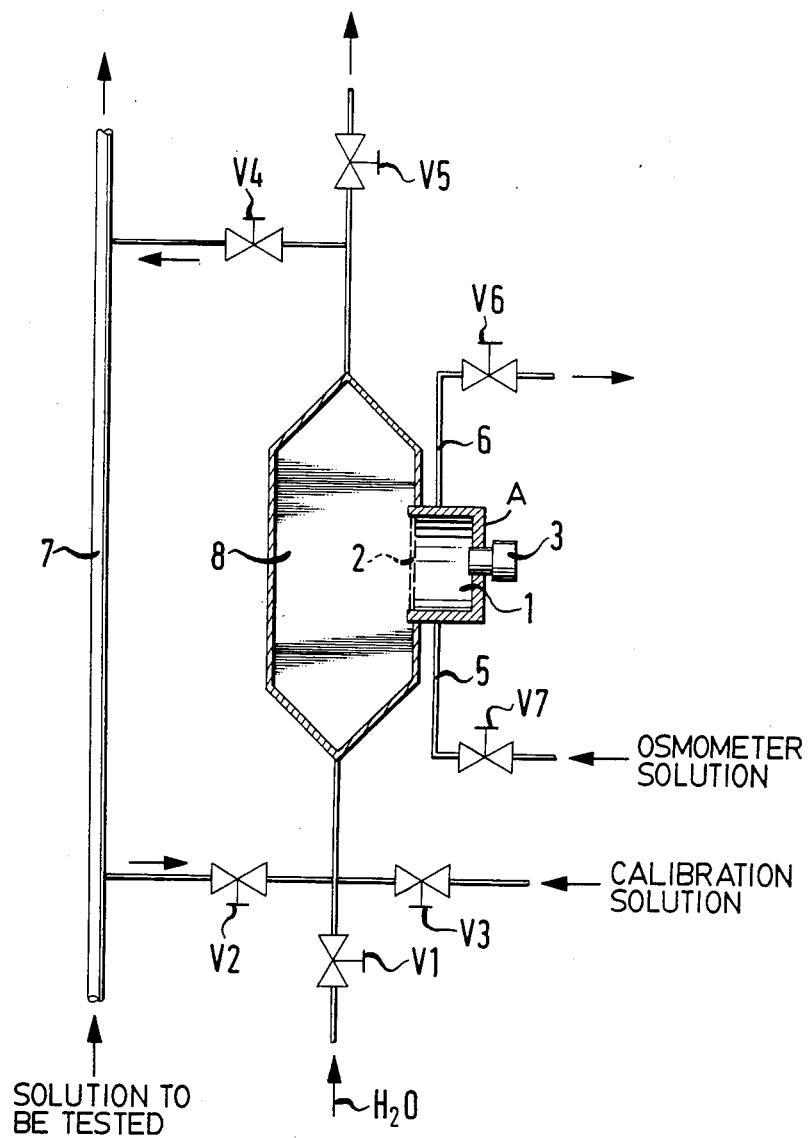
FIG. 2 shows a measurement head "A", consisting of an osmotic cell with a pressure measurement apparatus installed on an installation which contains the solution to be measured.

FIG. 2 shows a measurement head "A" of the type illustrated in FIGS. 1A and 1B, comprising an osmotic cell 1 and a pressure measurement apparatus 3 in use. An apparatus for the controlled volume change is not present in this embodiment, but there is a closable feed line 5 and a closable discharge line 6 for the osmometer solution.

For the determination of the concentration of dissolved substance in a solution in the line 7, first of all a solution suitable for the establishment of the working pressure $P_0$, e.g. distilled water, is admitted via open valves V1 and V5 and closed valves V2, V3 and V4 into a container 8, whereby the solution ($H_2O$) is brought into communication via a membrane 2 with the osmometer solution, which is in the osmotic cell 1. After the establishment and determination of the working pressure $P_0$, the solution to be tested is then admitted to the container 8 via open valves V2 and V4 or V5 and closed valves V1, V3 and possibly V5 or V4, whereupon the minimum pressure $P_{min}$ is established first of all, and then the final pressure $P_E$. During this measurement process, of course, the valves V6 and V7 are closed. For calibration, if necessary, a calibration solution can be admitted to the container 8 via the valve V3, with an appropriate setting of th other valves.

Figure 3A:
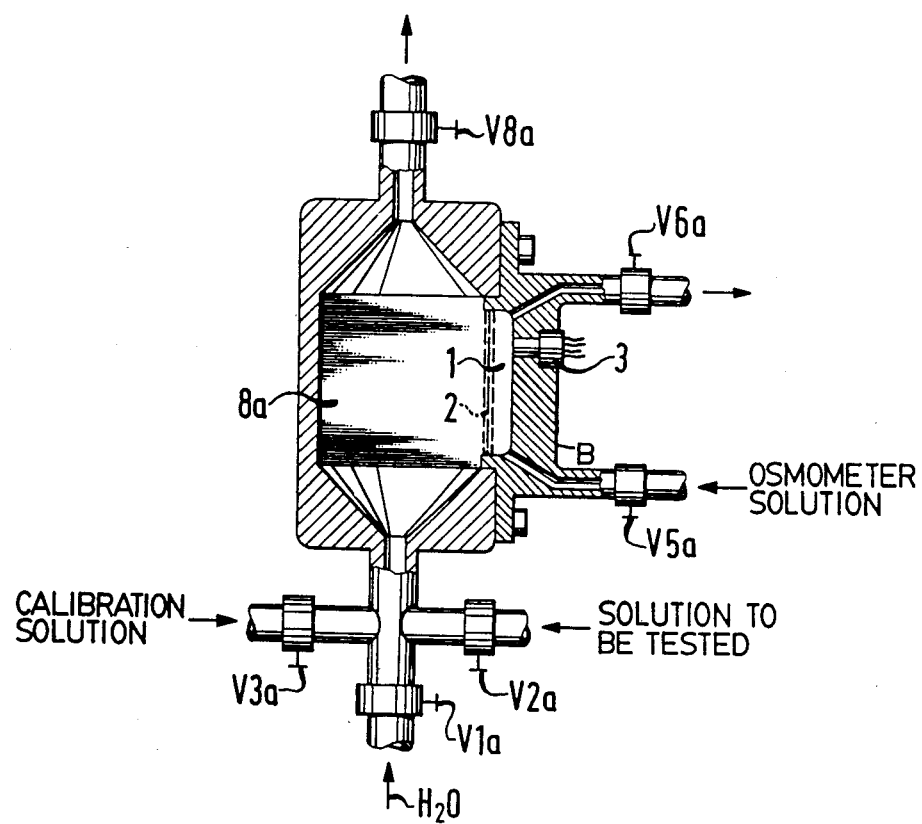
FIG. 3A shows a measurement head "B", consisting of an osmotic cell and a container adjacent to the cell.
Figure 3B:
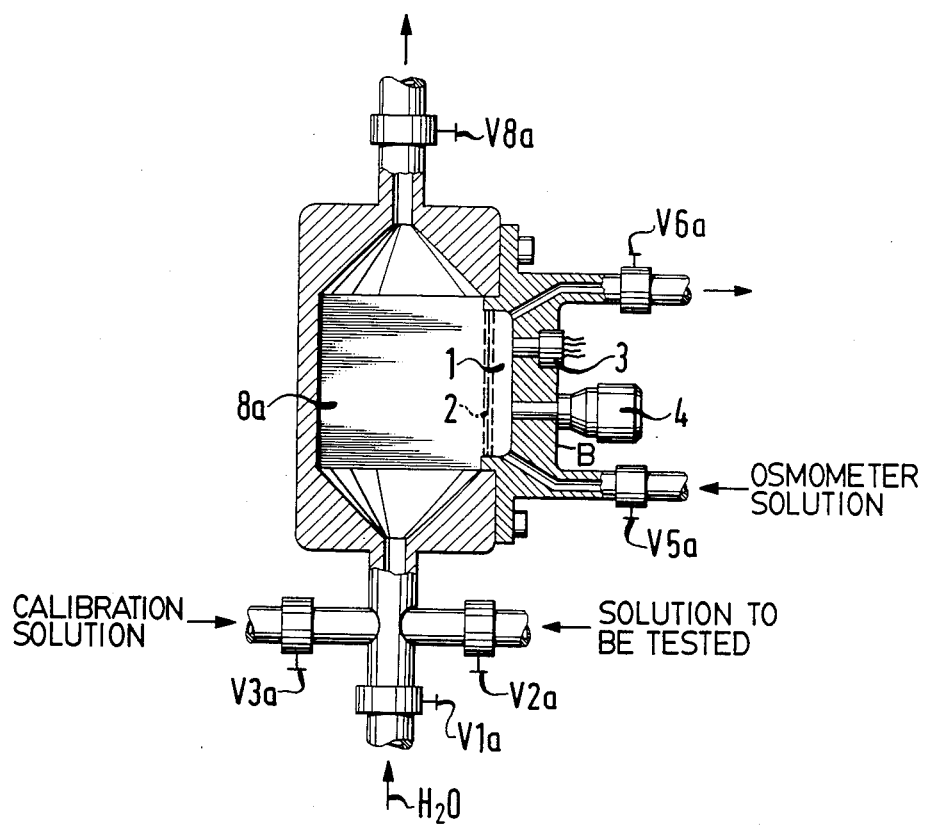
FIG. 3B shows a measurement head "B", consisting of an osmotic cell and a container adjacent to the cell, as well as a micrometer screw with a control rod.

FIG. 3 shows a measurement head "B" with an osmotic cell 1 and a membrane 2, containing a container 8a corresponding to the container 8 in FIG. 2. The valves V1a, V2a, V3a, V5a and V6a corrspond to the valves V1, V2, V3, V5 and V6 represented in FIG. 2. V8a is the outlet valve of the container 8a integrated into the measurement head. For the measurement head illustrated in FIG. 3, there is also a pressure measurement apparatus 3 with an electrical indicator, as well as an apparatus 4 for the controlled volume change of the osmotic cell 1 as described above in connection with measurement head "A" of FIGS. 1 and 2. Moreover, the several features described in combination with measurement head "A" can also be used in the measurement head "B" shown in FIGS. 3 and 4.

Figure 4:
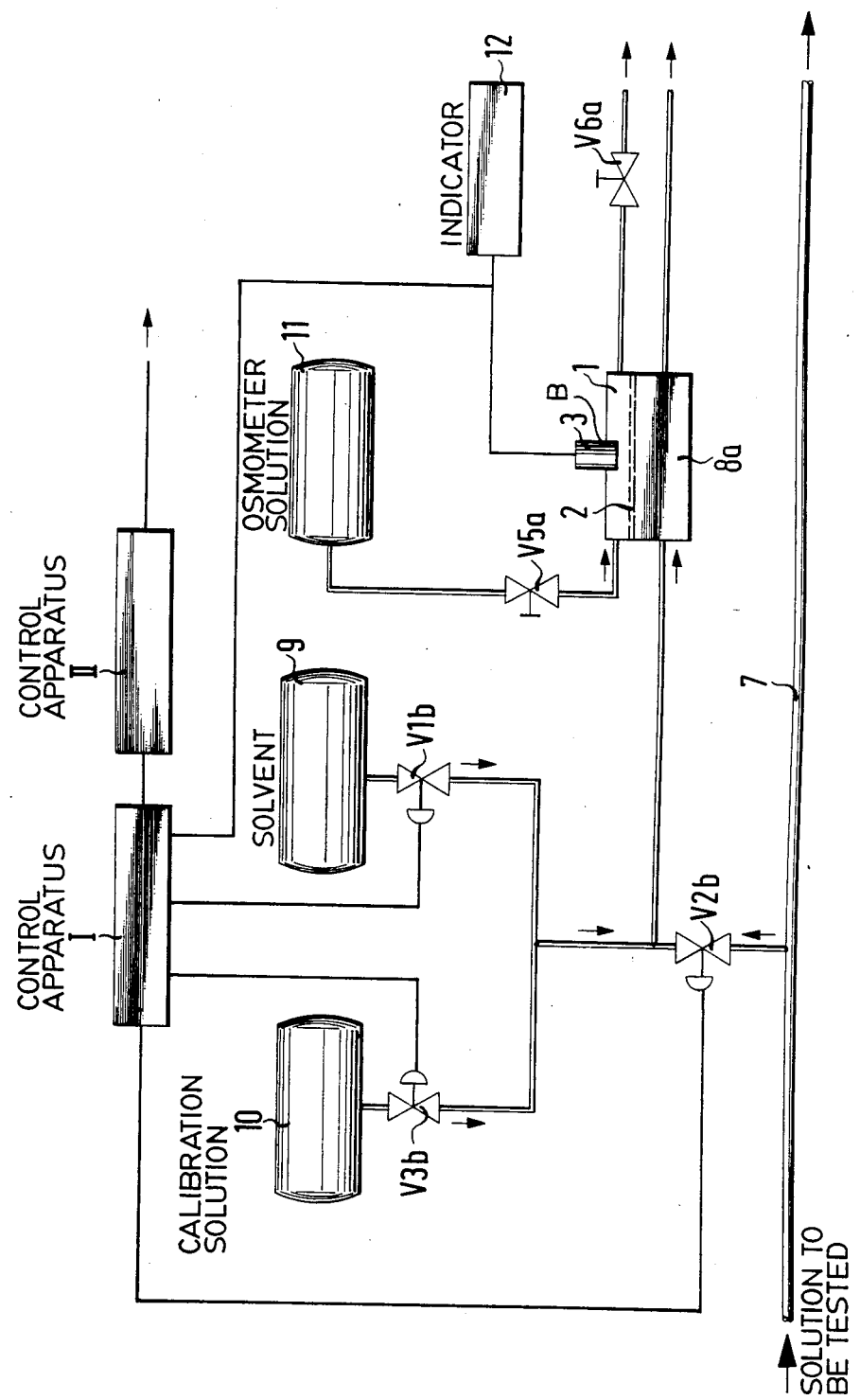
FIG. 4 shows an apparatus with measurement head "B" according to FIG. 3 with automatic control of the measurement process as well as a process control.

FIG. 4 shows an apparatus with a measurement head "B" of the type illustrated in FIG. 3, which is suitable for the determination of the concentration of substances in a solution flowing in line 7. The valves V1b, V2b and V3b correspond functionally with the valves V1a, V2a and V3a illustrated in FIG. 3, but they are designed as remote-control cutoff valves, which are electrically connected to the control apparatus I. By means of this control apparatus I, at pre-determined time intervals, solvent is fed in from the storage container 9 via the valve V1b (with valves V2b and V3b closed) into the container 8a to set the working pressure $P_0$, and then the solution to be tested is introduced from the line 7 via the valve V2b (with valves V1b and V3b closed). In addition, at longer time intervals, by means of the control apparatus I, the feed of calibration solutions can be tripped from the storage container 10 via the valve V3b (with valves V1b and V2b closed) into the container 8a. There is also a storage container 11 for the osmometer solution.

As also shown in FIG. 4, the electrical output signals from the pressure measurement apparatus 3 are displayed on an indicator 12 and taken over by the control apparatus I. By means of a control apparatus II, which is electrically connected to the control apparatus I, the process is controlled as a function of the measurement values determined.

The objects of this invention can be achieved through alternative processes which will be described in detail hereinafter.

The objects of this invention are achieved by a method which is identified as Method Ia below. This method consists of the use of the most rigid possible osmotic cells, as well as a membrane which exhibits the highest possible conductivity for the solvent and a sufficient retaining capability for the substances, and that, first of all, using a suitable solution brought into communication with the osmometer solution via the membrane as well as a suitable osmometer solution, a work pressure $P_0$ is established and determined, whereupon the solution brought into communication with the osmometer solution via the membrane is replaced sufficiently rapidly by the solution containing the substances, whereupon the minimum pressure $P_{min}$ established in the osmotic cell is determined, as well as the final pressure $P_E$ established in the osmotic cell after the subsequent pressure increase, whereby, on the basis of calibrated values, the concentration of the impermeable substance or substances in the solution to be tested is computed from the pressure difference $P_0 - P_E$ and the concentration of the permeable substance in the solution from the pressure difference $P_E - P_{min}$. The process can be conducted so that the concentration of impermeable ($C_{imp}°$) substances and permeable ($C_s°$) substances in the solution to be tested is determined by calibration of the measurement system with various solutions containing impermeable and permeable substances in different known concentrations, whereby care is to be taken in the determination of the permeable components that the calibration solutions contain the impermeable substance in approximately the same concentration as the solution to be tested, whereupon their concentration of permeable substance results from the graph $(P_E - P_{min}) = f(C_s°)$ and the concentration of impermeable substances from the graph $(P_0 - P_E) = g(C_{imp}°)$. $(P_0 - P_E) = g(C_{imp}°)$ represents in each case a straight line, while $(P_E - P_{min}) = f(C_s°)$ can deviate from the linear form, since $t_{min}$ is a function of mixing ratio $\sigma_s \cdot C_s° / C_{imp}°$.

The objects of the invention can be achieved alternatively by an alternative method identified as Method Ib. The method consists of using an osmotic cell which is as rigid as possible, and a membrane, which exhibits the highest possible conductivity for the solvent and a sufficient retention capability for the substances, and that first of all, using a suitable solution brought into communication via the membrane with the osmometer solution and a suitable osmometer solution, a working pressure $P_0$ is established, whereupon the solution brought into communication with the osmometer solution via the membrane is replaced sufficiently rapidly by the solution containing the substances, whereupon the minimum pressure $P_{min}$ established in the osmotic cell, the time $t_{min}$, within which the minimum pressure $P_{min}$ is achieved, the velocity constant $k_s$ for the exponential pressure increase after the minimum pressure, and the final pressure $P_E$ which is achieved after the pressure increase are determined, after which the concentration $C_s^\circ$ of the permeable substance can be computed from the equation:

$$P_E - P_{min} = \sigma_s \cdot RT \cdot C_s^\circ \cdot \exp(-k_s \cdot t_{min}) \tag{1}$$

with

R = 8.31434 J/°K. mol;
T = absolute temperature; and
$\sigma_s$ = reflection coefficient of s, and the concentration ($C_{imp}^\circ$) of the impermeable substance or substances is determined from the equation:

$$P_0 - P_E = RT \cdot C_{imp}^\circ \tag{2}$$

According to the principle of the invention, the osmotic cell to be used should be as rigid as possible, that is, an osmotic cell with a rigid wall and rigid membrane, so that during the execution of the process, the change of the volume of the osmotic cell is negligible. For this case, Equations 1 and 2 apply.

For the case, however, in which the membrane and the osmotic cell are not sufficiently rigid and the changes in the volume of the osmotic cell which occur during the determination are not negligible, the volumetric elastic modulus ($\epsilon = V\Delta P/\Delta V$) can be determined by means of a suitable apparatus, after which the concentration $C_s^\circ$ of the permeable substance can be obtained from the equation:

$$P_E - P_{min} = \frac{\epsilon}{\epsilon + RT \cdot C_{imp}^i} \cdot \sigma_s \cdot RT \cdot C_s^\circ \cdot \exp(-k_s \cdot t_{min}) \tag{3}$$

and the concentration $C_{imp}^\circ$ of the impermeable substance from the equation:

$$P_O - P_E = \frac{\epsilon}{\epsilon + RT \cdot C_{imp}^i} RT \cdot C_{imp}^\circ \tag{4}$$

The membrane to be used in both Methods Ia and Ib should exhibit the highest possible conductivity for the solvent and a sufficiently high retention capability for the substances or solutes of interest. The retention capability of the membrane is sufficient for the substances, if the exchange of the permeable substance through the membrane is delayed in relation to the exchange of the pure solvent via the membrane, so that during the exchange phase of the pure solvent, the exchange of the permeable substance is only minor. Moreover, if the exchange of the impermeable substance is delayed in relation to the exchange of the permeable substances so that during the exchange of the permeable substance, no notable exchange of the impermeable substance takes place. That is, if the velocity constant $k_s$ of the permeable substance is sufficiently large compared to that of the impermeable substance or if during the test practically no impermeable substance gets through the membrane. On the other hand, with the specified membrane, a substance is to be considered permeable in the sense of the invention if it is sufficiently delayed during the execution of the method in relation to the pure solvent, but gets through the membrane sufficiently rapidly in relation to the impermeable substance. Accordingly, a substance is to be considered impermeable in the sense of the invention if, during the performance of the method, practically none of it gets through the membrane. In this sense, accordingly, a substance can be practically impermeable, although the reflection coefficient $\sigma_s$ is less than 1, if its permeability ($k_s$) in the membrane is sufficiently low.

According to the invention, to set the working pressure $P_0$, a suitable osmometer solution is introduced into the osmotic cell, and a suitable solution is brought into communication with the osmotic cell via the membrane. The pure solvent (e.g. water) is suitable for use as the solution outside the osmotic cell. A suitable osmometer solution, on the other hand, is a solution in which there is an impermeable substance, so that as a result of the osmotic pressure difference across the membrane in the osmotic cell, the hydrostatic working pressure $P_0$ builds up. The concentration of the impermeable substance in the osmometer solution is thereby selected appropriately, i.e. a working pressure $P_0$ is to be selected so that in the subsequent determination of the substances, properly measurable differential pressures ($P_0 - P_E$) or ($P_E - P_{min}$) are obtained.

After the determination of the working pressure $P_0$ in the osmotic cell, the solution placed in communication with the osmotic solution via the membrane, e.g. the pure solvent, is replaced sufficiently rapidly by the solution containing the substances to be determined, whereupon the minimum pressure $P_{min}$ is established. Since this minimum pressure is determined by the concentration of the permeable substance in the solution (resulting from $P_E - P_{min}$), the replacement process of the two solutions must take place very rapidly in relation to the half-value time for the flow of the pure solvent through the membrane, which can be in the range of seconds.

In the performance of the alternative Method Ib according to the invention, in relation to the first Method Ia, the time $t_{min}$ from the beginning of the replacement process of the two solutions (solvent and solution to be tested) until the establishment of the minimum pressure $P_{min}$ must also be determined, as must the velocity constant $k_s$ for the pressure increase which takes place after the minimum pressure, which is a result of the permeation of the permeable substance through the membrane. Before the execution of Method Ib, in addition, the reflection coefficient $\sigma_s$, which is a material constant with a given membrane and a given solvent, must be determined. This is done by using calibration solutions indicated in the process described by E. Steudle and S. D. Tyerman (1983), "Determination of permeability coefficients, reflection coefficients and hydraulic conductivity of *Chara corallina* under the pressure probe: Effects of solute concentration", J. Membrane Biol. 75, 85–96, the contents of which are incorporated herein by reference. After that, the osmotic cell is initially placed in communication with the pure solvent, whereby the working pressure $P_0$ is established. Then a solution is applied, which contains only the permeable substance in a known concentration. From the pressure difference ($P_0 - P_{min}$), $\sigma_s$ results after a correction for the flow of the permeable substance.

If the solution to be tested contains only one each impermeable and permeable substance, when Methods Ia and Ib according to the invention are applied, the absolute concentration of these substances can either be determined by using calibration values or according to the above-mentioned equations.

If a single permeable substance, but more than one impermeable substance, is contained in the solution, the concentration of the permeable substance and the total concentration of the impermeable substance is determined. If, in addition to the impermeable substance or substances, there are several permeable substances in the solution, then this has no influence on the determination of the (total) concentration of the impermeable substance or substances from the difference $P_0 - P_E$.

The methods indicated by the invention can therefore be applied to solutions with very different substances dissolved in them. The selection of an appropriate membrane can be made by regarding certain substances in the solution as impermeable and others as permeable, in the sense of the definitions indicated by the invention. A particular embodiment of Methods Ia and Ib consists of computing the rate constant $k_s$ for the exponential pressure increase which occurs following the minimum pressure and the temporal change $$\left(\frac{d^2P}{dt^2}\right)_{min}$$

of the slope of pressure/time curves around the pressure minimum, and calculating the final pressure $P_E$ from the equation:

$$k_s \cdot k_w = \frac{1}{P_E - P_{min}} \left(\frac{d^2P}{dt^2}\right)_{min} \tag{4a}$$

whereby previously, for the osmotic cell (1) used, the rate constant $k_w$ has been computed for the pressure change up to the minimum.

The rate constant $k_w$ is a measure for the rate of water exchange through the membrane. $k_w$ can be measured from pressure/time curves using a solution which only contains an impermeable substance.

When the above-mentioned alternative embodiments of Ia and Ib are carried out, then $$\left(\frac{d^2P}{dt^2}\right)_{min}$$

can be determined graphically or by curve fitting by means of a computer. The latter method is preferable because it can be carried out more rapidly.

In another configuration of the above-mentioned embodiment variants, the rate constant $k_s$ is determined in advance for the solution to be tested and containing the substances. When the alternative embodiments are subsequently executed, the previously-determined value for $k_s$ (likewise the one for $k_w$) is only used for the calculation of $P_E$ in the determination (4a). This has the advantage that the determination of the concentrations can be made in a shorter period of time, since for this purpose, only the course of the pressure curve up to the end of the area needed for the determination of $$\left(\frac{d^2P}{dt^2}\right)_{min}$$

around the minimum must be used. This can lead to significantly shorter measurement times, since the exponential increase of the pressure curve which takes place just after the minimum is relatively the longest portion of the pressure curve.

The object of the invention is also alternatively achieved by the method described below and identified as Method II, which consists of the alternative Methods IIa and IIb. This process requires the most rigid possible osmotic cell, as well as a membrane with the greatest possible conductivity for the solvent and the greatest possible retaining capacity for the substances. Initially, using a suitable solution brought into communication with the osmometer solution via the membrane and a suitable osmometer solution, a working pressure $P_0$ is established. Whereupon, if the solution to be tested contains two substances, after replacement of the solution brought into communication with the osmometer solution via the membrane by the solution containing the two substances, from the pressure drop in the osmotic cell which occurs because of this replacement in this osmotic cell, the initial slope $$\left(\frac{dP}{dt}\right)_{t=0}$$

of the pressure time curve is determined, and with this measurement, based on calibration values or values from the equation:

$$\left(\frac{dP}{dt}\right)_{t=0} = -\frac{A_o}{V_o} \cdot Lp \cdot \epsilon \cdot RT(\sigma_1 \cdot C_1 + \sigma_2 \cdot C_2) \tag{5}$$

the result $$X_1 = \sigma_1 \cdot C_1 + \sigma_2 \cdot C_2 \tag{6}$$

is determined, whereby:
$A_o$ is the effective surface area of the membrane;
$V_o$ is the volume of the osmotic cell;
$Lp$ is the hydraulic conductivity of the membrane;
$\epsilon$ is the volumetric elastic modulus of the osmotic cell;
$R = 8.31434$ J/°K. mol;
$T$ is the absolute temperature;
$\sigma_1$ is the reflection coefficient of the substance No. 1;
$C_1$ is the concentration of the substance No. 1;
$\sigma_2$ is the reflection coefficient of the substance No. 2; and
$C_2$ is the concentration of substance No. 2, and that parallel to the determination of the resultant value $X_1$, according to the described method, another measurement is made by means of a second osmotic cell with a membrane with another retaining capability for the substances (Method IIa), whereby another result $$X_2 = \sigma_1' \cdot C_1 + \sigma_2' \cdot C_2 \tag{7}$$

is determined. The concentrations of the two substances are then computed by means of the two result values $X_1$ and $X_2$, or the other measurement is conducted by means of the second osmotic cell according to one of the Methods Ia or Ib, whereby a membrane with appropriate rejection properties for the substances is used so that, with regard to the membrane used, the one substance is permeable and the other substance is impermeable, and whereby it is sufficient that only the concentration of the permeable substance or the concentration of the impermeable substance be determined, and using the result $X_1$, the concentrations of both substances are calculated (Method IIb).

For the execution of the alternative Method IIa, according to which the resulting value $X_1$ and simultaneously the resulting value $X_2$ are determined, it must be guaranteed that the response times (time constants) of the osmotic cells are sufficiently small in relation to the time constant of the process to be observed. That is the case when the K-values of the osmotic cells:

$$K = \frac{A_o}{V_o} \cdot L_p \cdot \epsilon \cdot RT \tag{8}$$

are sufficiently large. Since with regard to the factors $A_o/V_o$, $L_p$ and $\epsilon$, it is a question of design-specific values of an osmotic cell or its membrane, it can be achieved by the selection of suitable osmotic cells. On the other hand, the practically linear course of the pressure/time curve for sufficiently short times after a change of solutions should be sufficiently long compared with the duration of the mixed phase, which is formed during the exchange of the two solutions in the measuring system.

The reflection coefficients $\sigma_1$ and $\sigma_2$ are to be determined in advance. For the determination of $\sigma_1$ or $\sigma_2$, the initial slope which the substance No. 1 or 2 of known concentration causes is compared with that which is obtained after the addition of an impermeable substance (in known concentration). In alternative Method IIa, the membranes of the two osmotic cells are to be selected so that the values for $\sigma_1$ and $\sigma'_1$ or $\sigma_2$ and $\sigma'_2$ are sufficiently different. The constant value K for a specified osmotic cell can be determined by calibration.

The short-term mixing of the solutions which occurs during the exchange of solutions in a container or in a pipeline can lead to a situation in which the initial pressure decrease in the osmotic cell is imprecisely defined. Only when the solutions have been completely switched will the linear portion of the pressure/time curve be reached, from which the initial slope for the execution of Method II can be determined.

If we overlook the variants of the Methods Ia and Ib, then alternative Method IIa makes possible a more rapid determination of the concentrations of the two substances than Methods Ia and Ib, since in the latter, the course of the total pressure curve must wait until the final value $P_E$ is reached. For this purpose, however, in the execution of Method IIa (as with the Method IIb), two osmotic cells are necessary. The execution of Method Ia or Ib, on the other hand, requires only a single osmotic cell each.

Even according to Method IIb, in which the parallel measurement is made via the determination of the pressure difference $(P_E - P_{min})$ or $(P_0 - P_E)$, a more rapid determination of the concentration of a substance is possible if the concentration of one of the substances is constant and only the concentration of the other substance is to be measured.

In addition, according to Methods IIa and IIb, the time at which a solution containing two substances arrives can be determined, for example, at the measurement point of a pipeline into which water initially flows. For this purpose, the determination of the sum $X_1$ (or $X_2$) is sufficient for the determination of the time.

Of course, if the primary interest is not in the determination of the concentration of the substances, but in the determination of the time of a change of concentration of a solution in a container or in a pipe, Method II can be used without a parallel measurement, that is, the pressure decrease in the osmotic cell is determined by means of only one osmotic cell. In this manner, an osmotic cell can be used as a control or alarm apparatus.

The determination of the time according to Method II is also possible when the initial slope $$\left(\frac{dP}{dt}\right)_{t=0}$$

does not display a linear dependence on the concentrations, which is possible in the range of very high concentrations, and can lead to a hyperbolic shape for the calibration curves. A non-linear dependence may primarily indicate a concentration dependence of the hydraulic conductivity of the membrane ($L_p$) or effects of unstirred layers. A determination of concentration according to Method II is possible in this case, by diluting the solution to be tested so that there is again a linear relationship or by calculating, from $(P_0 - P_E)$, first $C_{imp}°$, and then determining a calibration curve in the expected range of concentration of $C_s°$ with solutions which already contain the impermeable substance in the correct concentration.

Applications for the determination of the concentration of substances are specifically the determination of low-molecular, permeable substances and high-molecular, impermeable substances. One application, for example, is the determination of the concentration of (permeable) alcohol and (impermeable) sugar during alcoholic fermentation. Such a determination is important both for the production of alcoholic beverages and also for the production of industrial alcohol. The methods described by the invention are also applicable to the determination of blood alcohol levels in human beings.

Other applications are the determinations of the concentration of organic solvents in aqueous solutions, for example, of ethanol, methanol, propanol, esters, ether, acetone, etc., as required for certain chemical processes. Another area of application in the chemical industry is the determination of solvent residues, salts and other harmful substances in waste water.

The methods described by the invention can also be used for the monitoring of dialysis processes.

A special application for Method II, and possibly for the special variants of Methods Ia and Ib, lies in the rapid detection of a change in a solution, such as can occur in a brewery or in other sectors of the foods industry when there is a change between a cleaning agent, for example, water, and a product, for example, beer.

As a result of the rapid determination of the time of the solution change at a given point, product losses can be severely limited. Method II, moreover, can be applied in connection with only one osmotic cell as a warning system, for example, to detect leaks in tanks, pipelines, etc., on the basis of rapid changes in concentration.

For an apparatus for the execution of the methods described by the invention, a suitable measurement head, identified as measurement head "A" in FIGS. 1A and 1B, comprises an osmotic cell with a rigid wall, whose membrane delimits this cell at least partly on the outside, and which has a pressure measurement apparatus for the measurement of the hydrostatic pressure in the osmotic cell. Its membrane has the highest possible modulus of elasticity, the highest possible conductivity for the solvent, and a sufficiently high rejection capability for the substances in the solution to be tested.

The measurement head "A", for the execution of the method described by the invention, can be located on or in a container, or on or in a pipeline (or a bypass line), with the membrane turned towards the inside of the chamber into which, in an alternating fashion, the solution to be tested (or a diluted partial solution of the same) and the solution used to set the working pressure $P_0$ are introduced for the length of time required for the test.

Another measurement head, identified as measurement head "B", is suitable for the execution of the methods described by the invention in an apparatus for the determination of the concentration of substances dissolved in a solvent, which comprises an osmotic cell with a pressure measurement apparatus for the measurement of the hydrostatic pressure in the osmotic cell and a container, which is in communication with the osmotic cell, so that its inside is adjoined by the membrane of the osmotic cell. According to the invention, the osmotic cell has a rigid wall made of metal or plastic. The container is equipped with a feed and discharge line for the solution for the establishment of the working pressure $P_0$, for the solution to be tested and for the calibration solutions, if any, whereby the feed and discharge line as well as the inside of the container are designed so that the solutions fed into them can be introduced into the container as rapidly as possible. The membrane according to the invention also exhibits the highest possible modulus of elasticity, the highest possible conductivity for the solvent and a sufficiently high retention capacity for the substances in the solution to be tested. A hyperfiltration membrane is appropriate. The membrane of the measurement heads "A" or "B", according to the invention, can be a hollow fiber membrane. The inside of the fibers can thereby serve as an osmotic cell or, in the case of measurement head "B", as the container. Of course, bundles of hollow fibers can also be used.

With measurement head "B" (the measurement head with integrated container), the solutions to be brought into communication by means of the membrane with the osmometer solution, that is, the solution required to establish the working pressure $P_0$ and the solution to be tested, as well as any calibration solution, are introduced into the container. The feed line and the inside of the container are designed so that the exchange of the solutions takes place both completely and as rapidly as possible. Unstirred layers can be minimized by rapid, continual flushing with the solutions.

The osmotic cell appropriately exhibits a feed and discharge line for the osmometer solution. The inside of the osmotic cell should be kept as small as possible, since experience has shown that such a small size is most suitable for the achievement of high $\epsilon$-values for the cell. On the other hand, agitation (convection) of the osmometer solution during the measurement is desirable, to minimize effects caused by unstirred layers on the membrane surface. For this purpose, an osmotic cell can also be equipped with an agitator. The stirrer should take up as little space as possible, however. Such a stirrer preferably comprises a magnetic stirrer of the type comprising a small magnet or metallic object disposed within the osmotic cell and manipulated by a rotating magnetic field generated external to the osmotic cell. An alternative, in which no stirring is necessary, consists of designing the osmotic cell so that its dimensions are on the order of magnitude of the expected thicknesses of the unstirred layers.

Specifically for the execution of Methods Ia and Ib, it is also appropriate if the ratio of the volume of the osmotic cell to the effective surface of the membrane is as small as possible, thereby guaranteeing the most rapid possible exchange of the solvent and the permeable substances in the solution to be tested by the membrane. This ratio should be no greater than 0.2 mm. If the membrane is not sufficiently rigid, it has been shown to be appropriate to reinforce the membrane with metal grids.

With regard to a general control of the measurement heads "A" or "B", not only for rigidity of the osmotic cells, but also for the determination of the modulus of elasticity $\epsilon$ of the osmotic cell for the method, in which the determinations are made according to Equations 3 and 4, it is appropriate to provide an apparatus for the controlled volume change of the osmotic cell. With such an apparatus, for example, the volume of the osmotic cell can be very precisely varied within certain limits by inserting and extracting a control rod, and the change in volume can be measured by means of a micrometer. With a closed osmotic cell, this causes pressure changes which are detected by means of the pressure apparatus. With a known volume of the osmotic cell, the elasticity of the osmotic cell (the volumetric elastic modulus $\epsilon$, whereby $$\epsilon = V \frac{\Delta P}{\Delta V})$$

can be determined. An alternative procedure to determine is to use Equation 4. If $C_{imp}^i$ and $C_{imp}$ are known, $\epsilon$ can be evaluated, if $P_0 - P_E$ is measured.

In another embodiment of the measurement head "A" or "B", according to the invention, the pressure measurement apparatus emits electrical output signals, which are a measure of the concentration of the substances in the solution to be tested.

For the use of measurement head "A", which comprises an osmotic cell without an additional container for the solution to be tested, a suitable apparatus includes a container on which the measurement head is installed, delimiting the inside of the container with its membrane, and which can be filled as required with a solution for the establishment of the working pressure $P_0$, with the solution to be tested and, if necessary, with calibration solutions. Of course, the container can also be a pipeline.

A suitable apparatus for measurement head "B" is one in which there is a storage container in communication with the feed line for the container with the measurement head for the solution used to establish the working pressure $P_0$, and possibly for the calibration solution, and a storage container for the osmometer solution in communication with the feed line for the osmotic cell, and on which, moreover, there is a recipient or a pipeline for one containing the solution to be tested in communication with the feed line for the container of the measurement head "B".

If a measurement head "A" or "B" is used for the apparatus, whose pressure measurement device emits electrical signals, then the curve of the measurement values can be printed out.

The devices can be selected independently of the type of measurement head used and the type of method applied, and, therefore, independently of whether one or two measurement heads are used, and as a measurement apparatus which can be moved or installed at a fixed point, for example, as part of an installation for the execution of a given process, such as alcoholic fermentation. It may be appropriate to have a control apparatus for control of automatic operation of the device, whereby alternately at pre-determined intervals of time, the solution intended to establish the working pressure $P_0$ and the solution to be tested are charged into the container of the measurement head "B" or into the container, to which measurement head "A" is attached. If there are two measurement heads for the execution of Method II, then, of course, one measurement head "A" and one measurement head "B" can also be used.

Another very advantageous apparatus is one in which there is another control and/or monitoring apparatus which receives the electrical output signals of the measurement head "A" or "B" or, when Method II is used, of the measurement heads "A"—"A", "A"—"B", or "B"—"B", and uses them to control and or monitor processes which have an operational relationship to the concentration of the substances to be tested. In addition to a monitoring of the processes, certain desired values of the concentration of the substances can be electronically regulated during such processes. Such processes include, for example, alcoholic fermentation, in which the concentration of alcohol (permeable) and the concentration of sugar (impermeable) can give some indication of the status of the fermentation or the monitoring of solvent concentrations in waste water. When the method according to the invention is used, traditional analytical concentration determinations are no longer necessary. In the case of the application of Methods Ia and Ib, the cycle time in which the measurement can be repeated is a function of, on one hand, the test time which can be several minutes, and on the other hand, the processes themselves which are to be monitored. The test time is a function of the physical properties of the membrane (conductivity for the solvent and the dissolved substances), and of the measurement head "A" or "B" (volume/surface ratio of the osmotic cell; volumetric elastic modulus), and can therefore be adjusted to serve the measurement situation at hand.

In one series of applications, an algal cell, specifically an internodal cell of Characeen species, is suitable as an osmotic cell for the execution of the process according to the invention, whereby the hydrostatic pressure prevailing in the cell is measured by means of a pressure probe introduced into the cell. As a solution for the establishment of the working pressure $P_0$, distilled water or a suitable nutrient solution is used initially. After the determination of the working pressure $P_0$, the distilled water or the nutrient solution is replaced sufficiently rapidly by the aqueous solution containing the substance, and the concentrations of the substance are determined according to the method proposed by the invention.

EXPERIMENTAL DATA

Embodiments using an Algal Cell as the Osmotic Cell:

By means of an internodal cell of the alga *Chara corallina* as the osmotic cell, aqueous solutions were tested in which ethanol was dissolved as the permeable substance and sucrose as the impermeable substance in different concentrations. The measurement of the pressure in the algal cell was made by means of a pressure probe introduced into the cell. The alga *Chara corallina* is available from the Algensammlüng des Pflanzenphysiologischen Instituts der Universität Göttingen, Nikolaus-Berger-Weg, Göttingen, Federal Republic of Germany, and from the Culture Collection of Algae and Protocoa, 36 Story's Way, Cambridge, CB 30 DT, United Kingdom.

Figure 5:
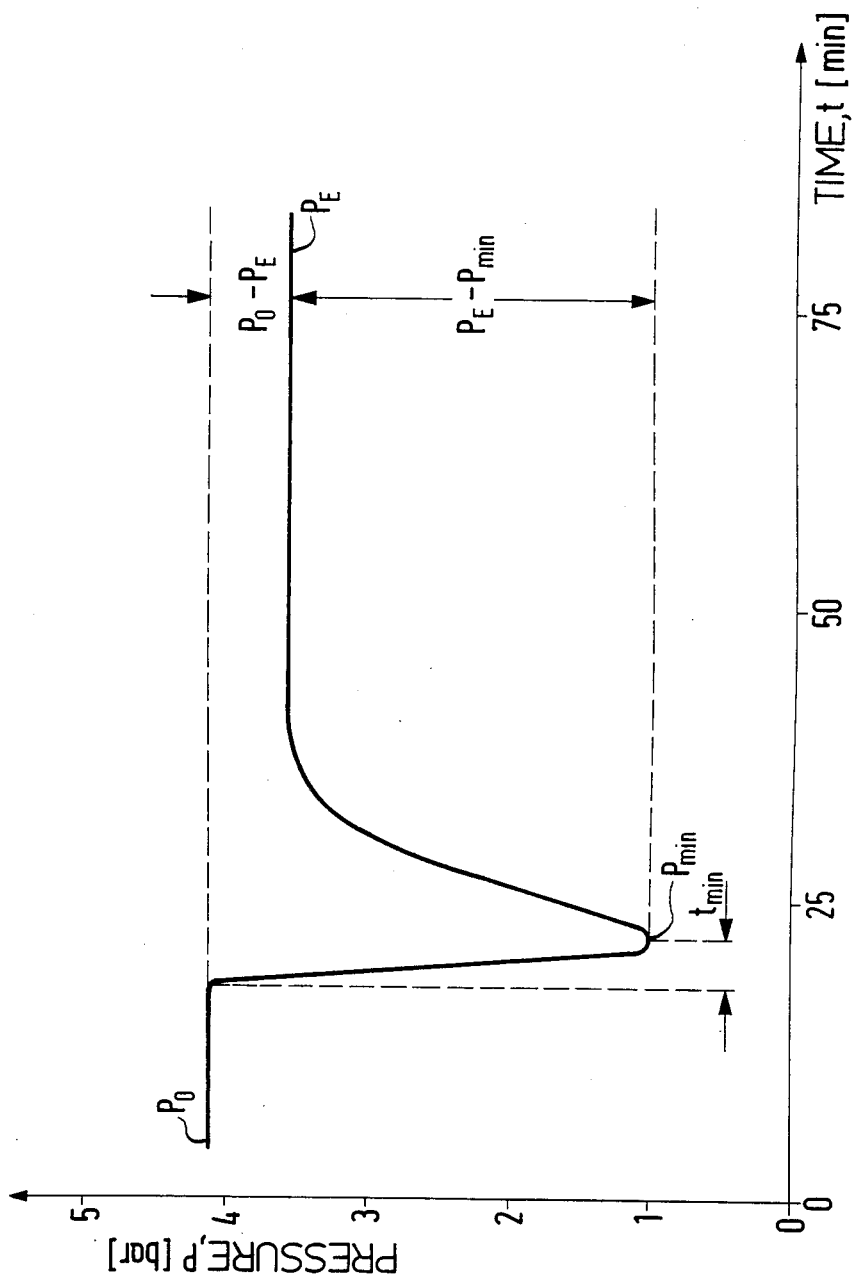
FIG. 5 shows the pressure curve in the osmotic cell during the measurement process.

For measurement purposes, the algal cell was located in a container, which was initially filled with distilled water for the establishment of the working pressure $P_0$. The distilled water was then very rapidly replaced by the solution to be tested, to initiate the measurement process, whereupon the pressure in the algal cell initially dropped to the minimum pressure $P_{min}$, and then reached the final pressure $P_E$, illustrated graphically in FIG. 5. The curve represented in FIG. 5 is the measurement curve for the embodiment 2b.

In embodiments 1a–1c, alternative Method Ib was used, and in embodiments 1d and 2e, alternative Method Ia was used.

Embodiment 1a

An aqueous solution was tested which contained 103.5 mMol ethanol (4.77 g/l) and 10 mMol sucrose (3.42 g/l). (In all embodiments, g/l is equivalent to grams per liter and mMol to mMol per liter).

The measurements:
$P_0 = 6.19$ bar
$P_{min} = 5.35$ bar
$P_E = 5.90$ bar
$t_{min} = 20.0$ seconds The reflection coefficient, which had been measured previously, was $\sigma_s = 0.32$.

The following values were calculated according to Equation (1) or Equation (2):
$C_s° = 106$ mMol ethanol
$C_{imp}° = 11.7$ mMol sucrose.

Embodiment 1b

The solution to be tested contained 103.5 mMol ethanol (4.77 g/l) and 20 mMol sucrose (6.85 g/l).
The measurements:
$P_0 = 6.12$ bar
$P_{min} = 5.10$ bar
$P_E = 5.62$ bar
$t_{min} = 21.2$ seconds
The calculated values were as follows:
$C_s° = 99$ mMol ethanol
$C_{imp}° = 20.2$ mMol sucrose.

Embodiment 1c

The solution to be tested contained 203.5 mMol ethanol (9.38 g/l) and 20 mMol sucrose (6.85 g/l).
The measurements:
$P_0 = 6.08$ bar
$P_{min} = 4.44$ bar
$P_E = 5.56$ bar
$t_{min} = 22.5$ seconds The calculated values:
$C_s° = 204$ mMol ethanol
$C_{imp}° = 21.0$ mMol sucrose.

Embodiments 1d and 1e

Figure 6B:
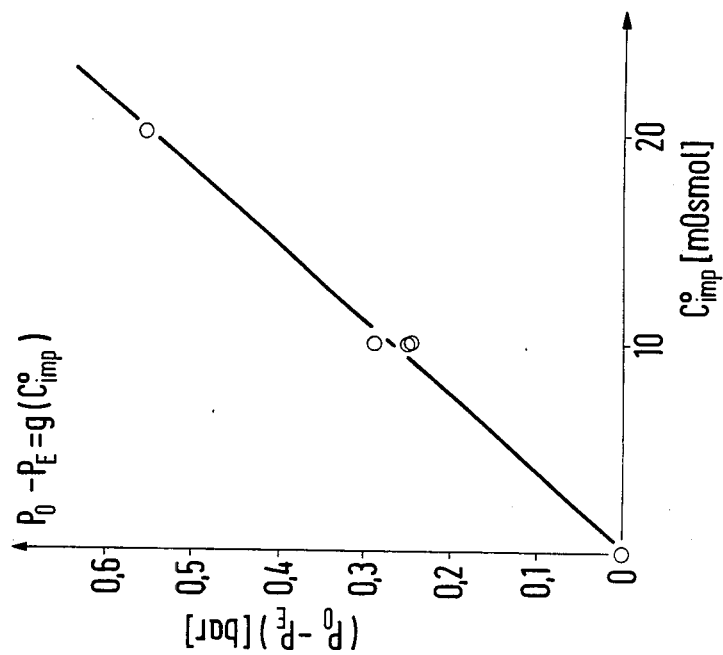
FIG. 6 shows calibration diagrams (Method Ia), measured by means of an algal cell.
Figure 6A:
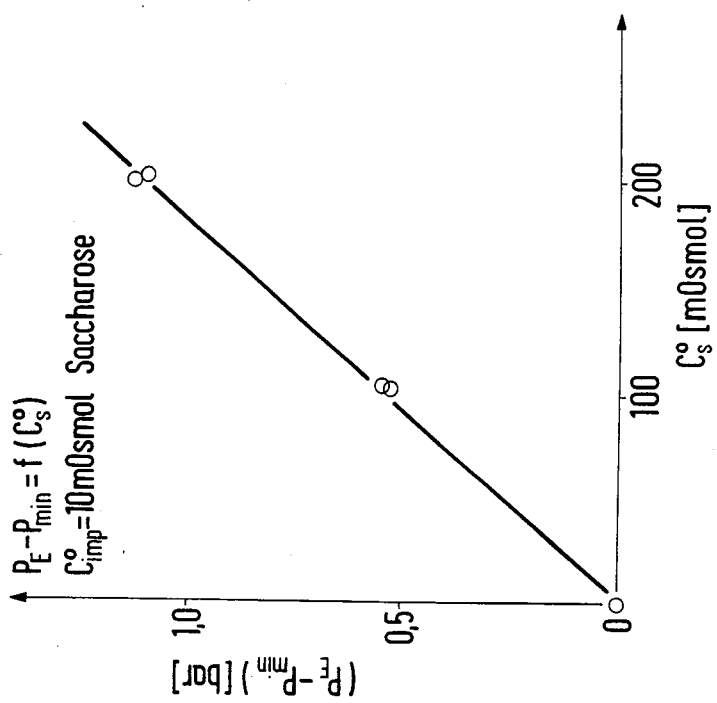

These embodiments relate to the Method Ia described by the invention, in which the concentrations of the substances in question are determined by using calibration values. For this purpose, the calibration curve identified as "A" in FIG. 6 was used for $(P_E - P_{min}) = f(C_s°)$ for the determination of the concentration $C_s°$ of the permeable substance (ethanol), and the calibration curve $(P_0 = P_E) = g(C_{imp}°)$ identified as "B" in FIG. 6 was used for the determination of the concentration $C_{imp}°$ of impermeable substance (sucrose). The calibration curve "A" had been measured by means of the algal cell for solutions containing 10 mMol of sucrose, but different concentrations of ethanol.

Embodiment 1d

The solution to be tested contained 103.5 mMol ethanol (4.77 g/l) and 10 mMol sucrose (3.42 g/l).
The measurement values:
$P_0 = 6.19$ bar
$P_{min} = 5.35$ bar
$P_E = 5.90$ bar
The values determined using the calibration curves in FIG. 6:
$C_s° = 102$ mMol ethanol
$C_{imp}° = 10.7$ mMol sucrose.

Embodiment 1e

The solution to be tested contained 201.5 mMol ethanol (9.28 g/l) and 10 mMol sucrose (3.42 g/l).
The measurement values:
$P_0 = 6.10$ bar
$P_{min} = 4.70$ bar
$P_E = 5.83$ bar
The values determined using the calibration curves in FIG. 6:
$C_s° = 206$ mMol ethanol
$C_{imp}° = 10.0$ mMol sucrose.

Embodiments using an Artificially Produced Osmotic Cell

Using a measurement head "B" of the embodiment illustrated in FIG. 3, aqueous solutions were tested, in which methanol had been dissolved as the permeable substance and sodium chloride as the impermeable substance. The measurement head consisted of a perspex housing. The membrane was an asymmetrical polyamide membrane (reverse osmosis membrane) with a separation limit of 50 Daltons, which had been inserted in the osmotic cell so that the separation layer of the membrane faced the pressure side, i.e., the separation layer was directed towards the osmotic cell. The ratio of volume to effective membrane surface of the osmotic cell was approximately 0.1 mm. The osmometer solution was an 0.15 (Examples 2a to 2e) or 0.25M (Examples 2f and 2g) solution of HEPES (N-2-Hydroxyethylpiperazine-N'-2-ethanesulfonic acid; MW=238.3 Dalton).

In embodiments 2a-2c, Method Ib as described by the invention was used, in which the concentration values of the substances in question are calculated.

Embodiment 2a

The solution tested contained 4 05 mMol methanol (12.98 g/l) and 20 mOsmol NaCl (0.58 g/l).
The measurements:
$P_0 = 4.10$ bar
$P_{min} = 2.34$ bar
$P_E = 3.65$ bar
$t_{min} = 255$ seconds
The reflection coefficient, which had been measured previously, was $\sigma_s = 0.38$.
The calculated values:
$C_s° = 394$ mMol methanol
$C_{imp}° = 18.5$ mOsmol NaCl.

Embodiment 2b

The solution to be tested contained 809 mMol methanol (25.92 g/l) and 20 mOsmol NaCl (0.58 g/l).
The measurement values:
$P_0 = 4.08$ bar
$P_{min} = 0.96$ bar
$P_E = 3.61$ bar
$t_{min} = 265$ seconds
The calculated values:
$C_s° = 800$ mMol methanol
$C_{imp}° = 19.1$ mOsmol NaCl.
The complete curve for this measurement is given in FIG. 5.

Embodiment 2c

The solution to be tested contained 810 mMol methanol (25.95 g/l) and 40 mOsmol NaCl (1.17 g/l).
The measurements:
$P_0 = 4.19$ bar
$P_{min} = 0.86$ bar
$P_E = 3.19$ bar
$t_{min} = 328$ seconds
The calculated values:
$C_s° = 804$ mMol methanol
$C_{imp}° = 40.7$ mOsmol NaCl.

In embodiments 2d and 2e, the Method Ia was used, in which the concentration values of the substances in question are determined by using calibrated values. For this purpose, the calibration curve identified as "A" in FIG. 7 was used for the determination of the concentration $C_s°$ of the permeable substance (methanol), and the calibration curve identified as "B" in FIG. 7 was used for the determination of the concentration $C_{imp}°$ of impermeable substance (NaCl). The calibration curve "A" had been measured by means of the measurement head for solutions containing 20 mOsmol NaCl, but different concentrations of methanol.

Embodiment 2d

The solution to be tested contained 405 mMol methanol (12.98 g/l) and 20 mOsmol NaCl (0.58 g/l).
The measurements:
$P_0 = 4.10$ bar
$P_{min} = 2.34$ bar
$P_E = 3.65$ bar
The values determined using the calibration curves in FIG. 7:
$C_s° = 404$ mMol methanol
$C_{imp}° = 18.3$ mOsmol NaCl.

Embodiment 2e

The solution to be tested contained 810 mMol methanol (25.95 g/l) and 40 mOsmol NaCl (1.17 g/l).

The measurements:
$P_0 = 4.19$ bar
$P_{min} = 0.86$ bar
$P_E = 3.19$ bar

Figure 7B:
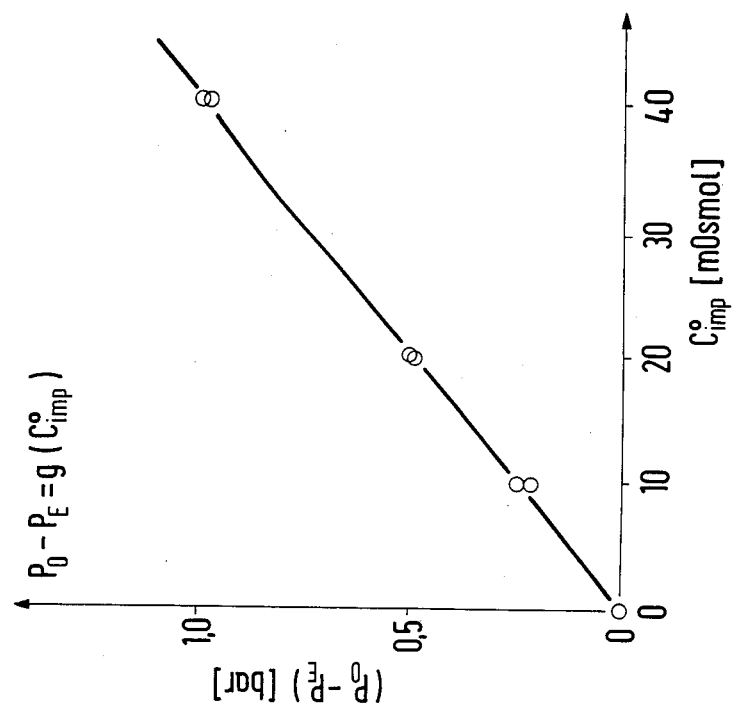
FIG. 7 shows calibration diagrams (Method Ia), measured by means of a measurement head "B" according to FIG. 3.
Figure 7A:
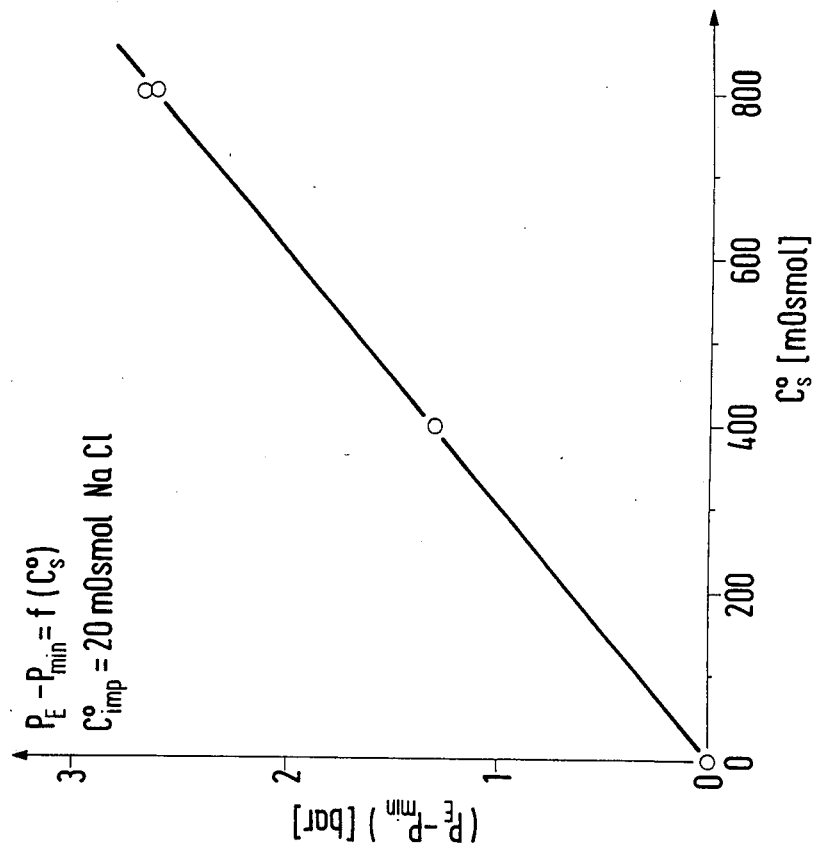

The values determined using the calibration curves in FIG. 7:
$C_s° = 812$ mMol methanol
$C_{imp}° = 40.7$ mOsmol NaCl.

Figure 8B:
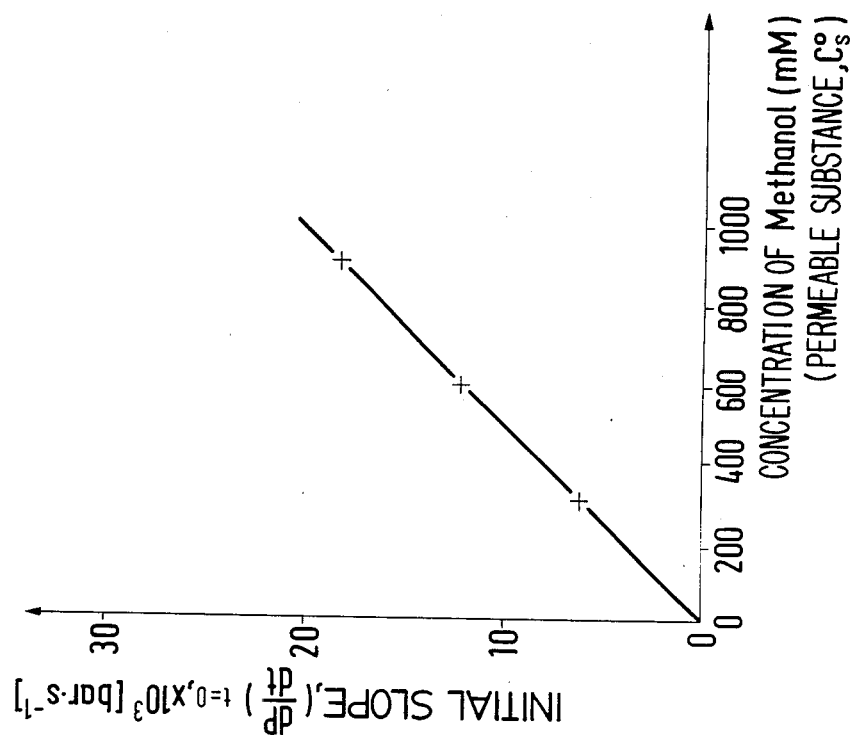
FIG. 8 shows calibration diagrams (Method II), measured by means of a measurement head "B" as shown in FIG. 3.
Figure 8A:
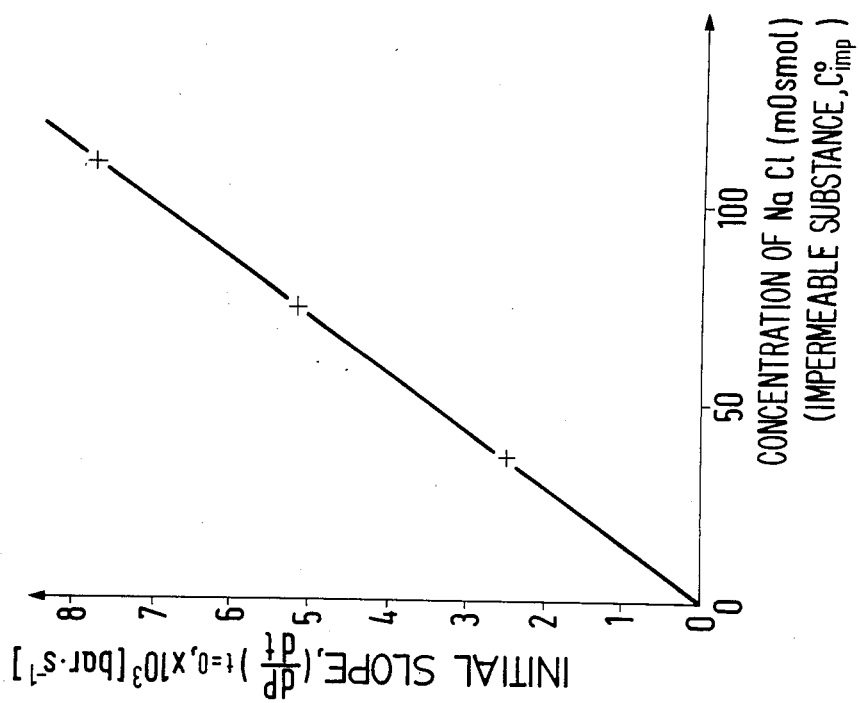

In the embodiments 2f and 2g, Method II was used, according to which $(dP/dt)_{t=0}$ was determined for the mixture (methanol and sodium chloride), and $(P_0 - P_E)$ for the impermeable substance (NaCl) was determined separately. From $(P_0 - P_E)$ it is possible to obtain the concentration of the impermeable substance, and, with the aid of the calibration diagram in FIG. 8A, its contribution to the measured $(dP/dt)_{t=0}$. The remainder for the measured initial slope gives, with the aid of FIG. 8B, the concentration of the permeable substance (methanol).

Embodiment 2f

The solution to be tested contained 304 mMol methanol (9.74 g/l) and 111 mOsmol NaCl (6.87 g/l).
The measurement values:
$P_0 - P_E = 271$ bar (t=20 C.) and
$(dP/dt)_{t=0} = 13.67 \cdot 10^{-3}$ bar·s$^{-1}$ gave, using the calibration diagrams 8A, B:
$C_s° = 295$ mMol, and
$C_{imp}° = 111.2$ mOsmol.

Embodiment 2g

The solution to be tested contained 901 mMol methanol (28.87 g/l) and 74 mOsmol NaCl (4.53 g/l).
The measurement values:
$P_0 - P_E = 1.85$ bar (t=20° C.) and
$(dP/dt)_{t=0} = 23.82 \cdot 10^{-1}$ bar·s$^{-1}$ gave, using the calibration diagrams 8A, B:
$C_s° = 908$ mMol, and
$C_{imp}° = 75.9$ mOsmol.

Embodiment 2h

Determination of $P_E$ from the temporal change of the slope in the vicinity of the minimum of pressure/time curves.

The test solution contained $C_s° = 494$ mOsmol ammonia as the permeable substance and $C_{imp}° = 16.2$ mOsmol mannitol as the impermeable substance.

$P_0 = 6.84$ bar; $k_s = 2.821 \cdot 10^{-3} s^{-1}$ $P_{min} = 6.16$ bar; $k_w = 3.793 \cdot 10^{-3} s^{-1}$ $$\left(\frac{d^2P}{dt^2}\right)_{min} = 4.0 \cdot 10^{-6} \text{ bar} \cdot s^{-2}; \quad \frac{\epsilon}{\epsilon + RT \cdot C_{imp}^i} = 0.946$$

From this, Equation (4a) gives:
$P_E - P_{min} = 0.37$ bar, and
$P_E = 6.53$ bar.
From $(P_0 - P_E) = 0.31$ bar, Equation (4) gives:
$C_{imp}° = 13.4$ mOsmol mannitol, compared to the specified 16.2 mOsmol. The measured $P_E$ value was $P_E = 6.49$ bar, compared to the calculated 6.53 bar.

The invention as described hereinabove in the context of the preferred embodiments is not to be taken as limited to all of the provided details thereof, since modifications and variations thereof may be made without departing from the spirit and scope of the invention.

What is claimed is:

1. In a process for the determination of the concentration of substances dissolved in a solvent by means of an osmotic cell with a pressure measurement apparatus for the measurement of the hydrostatic pressure in the osmotic cell, whereby an osmometer solution in the osmotic cell can be brought into communication via a membrane with a solution containing the substances, the improvement to said process comprising the steps of:
    selecting an osmotic cell which is as rigid as possible and which has a membrane which exhibits the maximum possible conductivity for the solvent and a sufficient rejection capability for the substances contained in the solution;
    introducing a suitable solution into communication with the osmometer solution by means of the membrane;
    establishing a working pressure $P_0$ in the osmotic cell, wherein the solution brought into communication with the osmometer solution by means of the membrane is replaced sufficiently rapidly by the solution containing the substances;
    determining an established minimum pressure $P_{min}$ in the osmotic cell and a final pressure $P_E$ established in the osmotic cell;
    establishing a difference between the working pressure $P_0$ and the final pressure $P_E$ in the osmotic cell, whereby the concentration of an impermeable substance or substances in the solution can be determined using predetermined calibration values; and
    determining the concentration of the permeable substance in the solution by determining a difference between the final pressure $P_E$ and the minimum pressure $P_{min}$ after calibration with solutions with known concentrations of the permeable substance.

2. The improved process according to claim 1, wherein a rate constant $k_s$ for an exponential pressure increase, which occurs after the minimum pressure and a temporal change $$\left(\frac{d^2P}{dt^2}\right)_{min}$$

of the slope of pressure/time curves in the vicinity of the pressure minimum are determined, and that the final pressure $P_E$ is determined from the equation:

$$k_s \cdot k_w = \frac{1}{P_E - P_{min}} \left(\frac{d^2P}{dt^2}\right)_{min}$$

whereby previously, for the osmotic cell used, the rate constant $k_w$ has been determined using an impermeable osmotic solute.

3. The improved process according to claim 2, including the step of predetermining the rate constant $k_s$ for the solution containing the substances to be investigated.

4. In a process for the determination of the concentration of substances dissolved in a solvent by means of an osmotic cell with a pressure measurement apparatus for the measurement of the hydrostatic pressure in the osmotic cell, whereby the osmometer solution in the osmotic cell can be brought into communication via a membrane with the solution, the improvement to said process comprising the steps of:

selecting an osmotic cell which is as rigid as possible and which has a membrane which exhibits the maximum possible conductivity for the solvent and a sufficient rejection capability for the substances contained in the solution;

introducing a suitable solution into communication with the osmometer solution by means of the membrane;

establishing a working pressure $P_0$ in said osmotic cell, wherein the solution brought into communication with the osmometer solution by means of the membrane is replaced sufficiently rapidly by the solution containing the substances;

determining a minimum pressure $P_{min}$ established in the osmotic cell;

determining a time $t_{min}$ in which, after the exchange of a two solutions, an minimum pressure $P_{min}$ is established;

determining the rate constant $k_s$ for the exponential pressure increase which takes place after the minimum pressure $P_{min}$ is established;

determining a final pressure $P_E$ which is established after the pressure increase;

determining the concentration $C_s^\circ$ of the permeable substance s contained in the solution according to the following equation:

$$P_E - P_{min} = \sigma_s \cdot RT \cdot C_s^\circ \cdot \exp(-k_s \cdot t_{min})$$

with
R = 8.31434 J/°K mol,
T = absolute temperature, and
$\sigma_s$ = reflection coefficient of s; and determining the concentration $C_{imp}^\circ$ of the impermeable substance in the solution from the following equation:

$$P_0 - P_E = RT \cdot C_{imp}^\circ$$

5. The improved process according to claim 4, wherein any significant changes occurring in the volume of the osmotic cell (the volumetric elastic modulus $\epsilon$ of the osmotic cell $$\left( \epsilon = V \frac{\Delta P}{\Delta V} \right) )$$

are corrected for according to which correction the concentration $C_s^\circ$ of the permeable substance results from the equation:

$$P_E - P_{min} = \frac{\epsilon}{\epsilon + RT \cdot C_{imp}^i} \cdot \sigma_s \cdot RT \cdot C_s^o \cdot \exp(-k_s \cdot t_{min})$$

with $C_{imp}^i$ = concentration of the osmometer solution and wherein the concentration $C_{imp}^\circ$ of the impermeable substance results from the equation:

$$P_0 - P_E = \frac{\epsilon}{\epsilon + RT \cdot C_{imp}^i} RT \cdot C_{imp}^o$$

6. The improved process according to claim 5, wherein the rate constant $k_s$ for the exponential pressure increase which occurs after the minimum pressure and the temporal change $$\left( \frac{d^2P}{dt^2} \right)$$

of the slope of pressure/time curves around the pressure minimum are determined, and that the final pressure $P_E$ is determined from the equation:

$$k_s \cdot k_w = \frac{1}{P_E - P_{min}} \left( \frac{d^2P}{dt^2} \right)_{min}$$

whereby previously, for the osmotic cell used, the rate constant $k_w$ has been determined from the pressure time course using an impermeable osmotic solute.

7. The improved process according to claim 6, including the step of predetermining a rate constant $k_s$ for the solution containing the substances to be investigated.

8. A method for the determination of the concentration of substances dissolved in a solvent by means of an osmotic cell with a pressure measurement apparatus for the measurement of the hydrostatic pressure in the osmotic cell, whereby the osmometer solution in an osmotic cell is placed in communication with the solution containing a substances by means of a membrane, wherein the most rigid possible osmotic cell and a membrane with the greatest possible conductivity for the solvent and the greatest possible rejection capability for the substances is used, wherein, initially, a working pressure $P_0$ is set with the use of the pure solvent placed in communication with the osmometer solution via the membrane and a suitable osmometer solution, whereupon, if the solution to be investigated contains two substances, after the replacement of the solvent placed in communication via the membrane with the osmometer solution by the solution containing the two substances, an initial slope $(dP/dt)_{t=0}$ of a pressure/time curve is determined from the pressure drop which occurs in the osmotic cell because of this replacement, and with these measurements, on the basis of calibrated values or from an equation $$\left( \frac{dP}{dt} \right)_{t=0} = -\frac{A_o}{V_o} \cdot Lp \cdot \epsilon \cdot RT(\sigma_1 \cdot C_1 + \sigma_2 \cdot C_2)$$

the result $$X_1 = \sigma_1 \cdot C_1 + \sigma_2 \cdot C_2$$

is determined, where:
$A_o$ is the effective surface of the membrane;
$V_o$ is the volume of the osmotic cell;
Lp is the hydraulic conductivity of the membrane;
$\epsilon$ is the volumetric elastic modulus of the osmotic cell;
R = 8.31434 J/°K mol;
T = absolute temperature;
$\sigma_1$ is the reflection coefficient of the substance 1;
$C_1$ is the concentration of the substance 1;
$\sigma_2$ is the reflection coefficient of the substance 2; and
$C_2$ is the concentration of the substance 2, and that parallel to the determination of the result $X_1$, either according to the described method, another measurement is made by means of a second osmotic cell with a membrane with another rejection capability for the substances, whereby another result $$X_2 = \sigma_1^1 \cdot C_1 + \sigma_2^1 \cdot C_2$$

is determined, and then the concentrations of the two substances are calculated by means of the two determined results $X_1$ and $X_2$.

9. The improved process according to claim 8, characterized by the fact that a constant value specified for an osmotic cell $$K = \frac{A_o}{V_o} \cdot Lp \cdot \epsilon \cdot RT$$

is determined by calibration.

10. An apparatus for use in the determination of the concentration of substances dissolved in a solvent, comprising: a housing having an osmotic cell with a membrane at least partly forming an outer boundary thereof and defining a chamber in said housing, said membrane being characterized by the highest possible modulus of elasticity, the highest possible conductivity for the solvent and a sufficient rejection capability for the substances in the solution to be tested and wherein said chamber has a ratio of chamber volume to effective area of said membrane of said osmotic cell which is no greater than 0.2 mm.

11. The apparatus for use in the determination of the concentration of substances dissolved in a solvent according to claim 10 wherein the membrane is a hyperfiltration membrane.

12. The apparatus for use in the determination of the concentration of substances dissolved in a solvent according to claim 10 wherein the membrane is a hollow fiber membrane.

13. The apparatus for use in the determination of the concentration of substances dissolved in a solvent according to claim 10 wherein the osmotic cell includes a feed line and a discharge line for introducing solution into and removing the same from said osmotic cell.

14. The apparatus for use in the determination of the concentration of substances dissolved in a solvent according to claim 10 wherein the chamber has a ratio of chamber volume to the effective area of the membrane of said osmotic cell of 0.2 mm, at most.

15. The apparatus for use in the determination of the concentration of substances dissolved in a solvent according to claim 10 wherein the osmotic cell includes a stirrer.

16. The apparatus for use in the determination of the concentration of substances dissolved in a solvent according to claim 10 wherein the membrane is reinforced by a metal grid.

17. The apparatus for use in the determination of the concentration of substances dissolved in a solvent according to claim 10 including, in combination, a container means into which said apparatus is mounted, wherein the inside of the container means adjacent to the membrane can be filled with a solution to set the working pressure $P_O$, with the solution to be tested or with calibration solutions.

18. The apparatus for use in the determination of the concentration of substances dissolved in a solvent according to claim 17 including one or more storage containers in communication with the container into which the apparatus is mounted, said one or more storage containers being adapted to contain therein the osmometer solution, or the solution to be tested.

19. The apparatus for use in the determination of the concentration of substances dissolved in a solvent according to claim 18 including automatic control means for selectively introducing substances contained in the one or more storage containers into the container into which the apparatus is mounted.

20. The apparatus for use in the determination of the concentration of substances dissolved in a solvent according to claim 19 including further control and monitoring apparatus means responsive to the signal generated by the pressure measuring apparatus means and adapted to control the transfer of the contents of the one or more storage containers into the container into which the apparatus is mounted.

21. An apparatus for use in the determination of the concentration of substances dissolved in a solvent comprising:
a container having means for the introduction of a solution thereinto, and the discharge of said solution therefrom;
a housing having an osmotic cell with a membrane at least partly forming an outer boundary of said housing, said membrane being in communication with the aforesaid container;
said osmotic cell defining a chamber in said housing;
said membrane being characterized by the highest possible modulus of elasticity, the highest possible conductivity for the solvent and a sufficient rejection capability for the substances in the solution to be tested and wherein said chamber has a ratio of chamber volume to effective area of said membrane of said osmotic cell which is no greater than 0.2 mm.

22. The apparatus for use in the determination of the concentration of substances dissolved in a solvent according to claim 21 wherein the membrane is a hyperfiltration membrane.

23. The apparatus for use in the determination of the concentration of substances dissolved in a solvent according to claim 21 wherein the membrane is a hollow fiber membrane.

24. The apparatus for use in the determination of the concentration of substances dissolved in a solvent according to claim 21 wherein the osmotic cell includes a feed line and a discharge line for introducing solution into and removing the same from said osmotic cell.

25. The apparatus for use in the determination of the concentration of substances dissolved in a solvent according to claim 21 wherein the osmotic cell includes a stirrer.

26. The apparatus for use in the determination of the concentration of substances dissolved in a solvent according to claim 21 wherein the membrane is reinforced by a metal grid.

27. The apparatus for use in the determination of the concentration of substances dissolved in a solvent according to claim 10 wherein the chamber being of a first predetermined volume, said housing further including means by which a measurable change in the predetermined volume can be effected and pressure measuring apparatus for generating a signal indicative of hydrostatic pressure changes within said chamber.

28. The apparatus for use in the determination of the concentration of substances dissolved in a solvent according to claim 21 wherein the chamber being of a first predetermined volume; said housing further including means by which a measurable change in the first predetermined volume can be effected and pressure measuring apparatus means for generating a signal indicative of hydrostatic pressure changes within the said chamber.

29. In a process for the determination of the concentration of substances dissolved in a solvent by means of an osmotic cell with a pressure measurement apparatus for the measurement of the hydrostatic pressure in the osmotic cell, whereby an osmometer solution in the osmotic cell can be brought into communication via a membrane with a solution containing the substances, the improvement to said process comprising the steps of:

selecting an osmotic cell which is as rigid as possible and which has a membrane which exhibits the maximum possible conductivity for the solvent and a sufficient rejection capability for the substances contained in the solution;

introducing a suitable solution into communication with the osmometer solution by means of the membrane;

establishing a working pressure $P_O$ in the osmotic cell, wherein the solution brought into communication with the osmometer solution by means of the membrane is replaced sufficiently rapidly by the solution containing the substances;

determining an established minimum pressure $P_{min}$ in the osmotic cell and a final pressure $P_E$ established in the osmotic cell;

establishing the difference between the working pressure $P_O$ and the final pressure $P_E$ is the osmotic cell, whereby the concentration of an impermeable substance or substances in the solution can be determined using predetermined calibration values; and determining the concentration of the permeable substance in the solution by determining the difference between the final pressure $P_E$ and the minimum pressure $P_{min}$ after calibration with solutions with known concentrations of the permeable substance, wherein a rate constant $k_s$ for an exponential pressure increase, which occurs after the minimum pressure and a temporal change $$\left( \frac{d^2P}{dt^2} \right)_{min}$$

of a slope of pressure/time curves in the vicinity of the minimum pressure are determined, and that the final pressure $P_E$ is determined from the equation:

$$k_s \cdot k_w = \frac{1}{P_E - P_{min}} \left( \frac{d^2P}{dt^2} \right)_{min}$$

whereby previously, for the osmotic cell used, the rate constant $k_w$ has been determined using an impermeable osmotic solute.

30. The improved process according to claim 28, including the step of predetermining a rate constant $k_s$ for the solution containing the substances to be investigated.

* * * * *